United States Patent
Furnish et al.

(12) 
(10) Patent No.: US 6,254,535 B1
(45) Date of Patent: Jul. 3, 2001

(54) BALL AND SOCKET CORONARY STABILIZER

(75) Inventors: Gregory R. Furnish, Lawrenceville; Christopher S. Looney, Roswell, both of GA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 08/792,151

(22) Filed: Jan. 31, 1997

Related U.S. Application Data

(63) Continuation-in-part of application No. 08/719,354, filed on Sep. 25, 1996, now Pat. No. 6,132,370, which is a continuation-in-part of application No. 08/639,214, filed on Apr. 26, 1996.

(51) Int. Cl.[7] .............. A61B 17/00; A61B 1/32
(52) U.S. Cl. ............... 600/213; 600/215; 600/235
(58) Field of Search .................. 600/201, 210, 600/213, 214, 217, 226–228, 234, 235, 37, 229, 231–233; 128/898; 269/3, 6; 81/391, 58.2, 59.1, 177.75

(56) References Cited

U.S. PATENT DOCUMENTS

| | | | |
|---|---|---|---|
| 569,839 | * 10/1896 | Roeloffs | 600/213 |
| 2,693,795 | 11/1954 | Grieshaber | 600/213 |
| 2,863,444 | 12/1958 | Winsten | 600/214 |
| 3,409,013 | 11/1968 | Berry | 600/201 X |
| 3,882,855 | 5/1975 | Schulte et al. | 600/201 X |
| 3,943,592 | 3/1976 | Bhaskar et al. | 600/240 X |
| 4,052,980 | * 10/1977 | Grams et al. | 600/211 X |
| 4,114,401 | * 9/1978 | Van Hoose | 81/177.75 X |

(List continued on next page.)

FOREIGN PATENT DOCUMENTS

| | | |
|---|---|---|
| 2216893 | 2/1999 | (CA) . |
| 90 04 513 | 6/1990 | (DE) . |
| 630 629 | 12/1994 | (EP) . |
| 668 058 | 8/1995 | (EP) . |
| 1019217 | 10/1952 | (FR) . |

(List continued on next page.)

OTHER PUBLICATIONS

"Cardiac Retractor for Coronary Bypass Operations," John A. Rousou, MD, et al., *The Annals of Thoracic Surgery*, 1991, 52: 877–78.

"A New Retractor to Aid in Coronary Artery Surgery," A.J. DelRossi, MD, G.M. Lemole, MD, *The Annals of Thoracic Surgery*, vol. 36, No. 1, 101–02, Jul. 1983.

"New Helper Instrument in Cardiac Surgery," D. Roux, MD, et al., *The Annals of Thoracic Surgery*, 1989, 48: 595–6.

"Aortic Spoon–Jaw Clamp for Aorta–Saphenous Vein Anastomosis," Francis Robicsek, M.D., *Journal of Cardiac Surgery*, 1995; 10:583–585.

(List continued on next page.)

*Primary Examiner*—Denise Pothier
(74) *Attorney, Agent, or Firm*—Richard D. Allison; Thomas J. DesRosier

(57) ABSTRACT

An apparatus for stabilizing a predetermined area on a heart or other organ of a patient to enable a surgical procedure, the apparatus comprising a bifurcated member having two elongated prongs and an elongated handle segment pivotally and rotatably attached to the bifurcated member. The handle segment can be movably attached to a rib retractor or other surgical device so that a person is not required to hold the handle segment. The preferred embodiment of the apparatus of the present invention further comprises a device to lock or frictionally hold the bifurcated member in a desired position both on the organ and relative to the handle segment during the surgical procedure.

30 Claims, 5 Drawing Sheets

U.S. PATENT DOCUMENTS

| | | | |
|---|---|---|---|
| 4,457,300 | * 7/1984 | Budde | 600/228 |
| 4,461,284 | 7/1984 | Fackler | 128/20 |
| 4,616,634 | 10/1986 | Vargas Garcia | 600/210 |
| 4,616,635 | 10/1986 | Caspar et al. | 128/20 |
| 4,637,377 | 1/1987 | Loop | 128/1 |
| 4,726,356 | 2/1988 | Santilli et al. | 128/20 |
| 4,949,707 | 8/1990 | LeVahn et al. | 600/228 X |
| 4,973,300 | 11/1990 | Wright | 600/37 |
| 5,133,724 | * 7/1992 | Wilson, Jr. et al. | 606/151 |
| 5,167,223 | * 12/1992 | Kores et al. | 600/232 |
| 5,201,325 | * 4/1993 | McEwen et al. | 600/202 X |
| 5,222,976 | 6/1993 | Yoon | 606/223 |
| 5,318,013 | 6/1994 | Wilk | 600/225 X |
| 5,337,736 | 8/1994 | Reddy | 600/217 |
| 5,429,118 | 7/1995 | Cole et al. | 600/121 |
| 5,449,374 | 9/1995 | Dunn et al. | 600/214 X |
| 5,498,256 | 3/1996 | Furnish | 606/1 |
| 5,509,890 | 4/1996 | Kazama | 600/37 |
| 5,518,503 | 5/1996 | Rooney et al. | 600/240 |
| 5,529,571 | 6/1996 | Daniel | 600/213 X |
| 5,558,621 | 9/1996 | Heil | 600/201 X |
| 5,609,565 | * 3/1997 | Nakamura | 600/229 |
| 5,727,569 | * 3/1998 | Benetti et al. | 128/898 |
| 5,749,892 | * 5/1998 | Vierra et al. | 600/204 |
| 5,782,746 | 7/1998 | Wright | 600/37 |
| 5,795,291 | * 8/1998 | Koros | 600/232 |
| 5,875,782 | 3/1999 | Ferrari et al. | 128/898 |
| 5,876,332 | * 3/1999 | Looney | 600/227 |
| 5,888,247 | 3/1999 | Benetti | 623/66 |
| 5,891,018 | * 4/1999 | Wells | 600/226 |
| 5,894,843 | 4/1999 | Benetti et al. | 128/898 |
| 5,904,650 | * 5/1999 | Wells | 600/226 |
| 6,036,641 | * 3/2000 | Taylor et al. | 600/235 X |

FOREIGN PATENT DOCUMENTS

| | | | |
|---|---|---|---|
| 2233561 | * 1/1991 | (GB) | 600/234 |
| WO 87/04081 | 7/1987 | (WO) . | |
| WO 94/14383 | 7/1994 | (WO) . | |
| WO 95/17127 | 6/1995 | (WO) . | |
| WO 97/10753 | 3/1997 | (WO) . | |
| WO 98/27869 | 7/1998 | (WO) . | |

OTHER PUBLICATIONS

"Technique of Dissecting the Internal Mammary After Using the Moussalli Bar," R.I. Hasan, et al. *European Journal of Cardiothoracic Surgery*, 4:571–572, 1990.

"Self–Retaining Epicardial Retractor for Aortocoronary Bypass Surgery," Victor Parsonnet, MD, et al., *The Journal of Thoracic and Cardiovascular Surgery*, 629–30, 1979.

"A New Internal Mammary Artery Retractor," M. Bugge, *Thoracic Cardiovascular Surgeon* 38, 316–17 (1990).

"A Simple, Inexpensive Method of Heart Retraction During Coronary Artery Bypass Surgery," G.D. Angelini, MD, M.H., F.R.C.S., *The Annals Thoracic Surgery* 46:246–47, Aug. 1988.

A New Device for Exposing the Circumflex Coronary Artery, Akio Matsuura, MD, et al., *The Annals of Thoracic Surgery* 1995; 59:1249–50.

"Correspondance and Brief Communications," *Archives of Surgery*, vol. 115, 1136–37, Sep. 1980.

"Internal Mammary Artery Dissection: A Three Dimensional Sternal Retractor", D. Roux, MD, et al., *Journal Cardiovasic Surgery*, 30, 996–97, 1989.

"Off–Bypass Coronary Bypass Grafting Via Mimithoracotomy Using Mechanical Epicardial Stabilization," Jochen Cremer, MD, et al., *The Annals of Thoracic Surgery* 1997; 63:s79–83.

"Single Coronary Artery Bypass Grafting—A Comparison Between Minimally Invasive 'Off Pump' Techniques and Conventional Procedures," Johannes Bonatti, et al., *European Journal of Cardio–Thoracic Surgery*, 14 (Suppl. I) (1998) s7–s12.

"Less Invasive Coronary Surgery: Consensus From the Oxford Meeting," Stephen Westaby, FRCS, and Federico J. Benetti, MD, *The Annals of Thoracic Surgery* 1996; 62:924–31.

"Mini–Sternotomy for Coronary Artery Bypass Grafting," Kit V. Arom, MD, PhD, et al., *The Annals of Thoracic Surgery* 1996; 61:1271–2.

"Limited Access Myocardial Revascularization," Denton A. Cooley, MD, Texas Heart Institute Journal, vol. 23, No. 2, 1996.

"Mini–Sternotomy for Coronary Artery Bypass Grafting," *The Annals of Thoracic Surgery*, 1996; 62:1884–85.

"The Cardiac Rag—Simple Exposure of the Heart," Michael M. Bedellino, MD, et al., *Texas Heart Institute Journal*, vol. 15, No. 2, 1988, 134–35.

"Fabric Heart Retractor for Coronary Artery Bypass Operations," Shigeru Kazama, MD, et al., *The Annals of Thoracic Surgery* 1993; 55:1582–3.

"Minimally Invasive Coronary Artery Bypass Grafting," Antonio M. Calafiore, MD, et al., *The Annals of Thoracic Surgery*, 1996; 62:1545–8.

"Improved Visualization of the Internal Mammary Artery With a New Retractor System," John Pittman, MD, et al., *The Annals of Thorac Surg*, 1989; 48:869–70.

"A Modified Sternal Retractor," Nelson Ancalmo, MD, and John L. Ochsner, MD, Aug. 8, 1975.

"A Versatile Retractor for Use in Harvesting the Internal Mammary Artery and Performing Standard Cardiac Operations," Steven J. Phillips, MD, and Marge Core, RN, *The Journal of Thoracic Surgery*, 1989; 97: 633–35.

"Surgical Management of Disease Intracavitary Coronary Arteries," John L. Ochsner, MD and Noel L. Mills, MD, *The Annals of Thoracic Surgery*, vol. 38, No. 4, 356–62 (Oct. 1984).

"Technique of Internal Mammary—Coronary Artery Anastomosis," *The Journal of Cardiovascular Surgery*, 78: 455–79, 1979.

"Graduated Probes for Coronary Bypass Surgery," George E. Green, MD, *The Journal of Thoracic and Cardiovascular Surgery*, vol. 68, No. 3, 424–27 (Sep. 1974).

"A Modified Sternal Retractor for Exposure of the Internal Mammary Artery," Peter P. McKeown, MB,BS, et al. *The Society of Thoracic Surgeons*, 1980.

"A New Concept in Sternal Retraction: Applications for Internal Mammary Artery Dissection and Valve Replacement Surgery," Aurelio Chaux, MD, and Carlos Blanche, MD, *The Annals of Thoracic Surgery*, 473–74, Oct. 1986. The Japanese Journal of Thoracic Surgery, 1989, vol. 42, No. 2 (translation of summary included).

"Tecnica Operatoria," Minerva Cardioangiologica, vol. 23—N. 6–7 (1975) (translation of summary included).

"Microsurgery: The New Frontier," V. Mueller, 1968.

"Neurosurgical Instruments," V. Mueller, Untitled Medical Device Catalog, 117–118, 1988.

"Heart Retractor for Use in Anastomosis in Coronary Artery By–Pass Surgery," *Japanese Journal of Thoracic Surgery*, vol. 40, No. 1, 1987 (translation of summary included).

Aesculap® General Surgical Catalogue (C–214730), Feb. 1983 (4 pages).

* cited by examiner

BALL AND SOCKET CORONARY STABILIZER

This application is a continuation-in-part application of application Ser. No. 08/719,354, filed Sep. 25, 1996, U.S. Pat. No. 6,132,370 which is a continuation-in-part application of application Ser. No. 08/639,214, filed Apr. 26, 1996, which is pending.

BACKGROUND OF THE INVENTION

1. Field of the Invention

This invention relates to an apparatus for stabilizing a predetermined area of the body during surgical intervention, which better enables a surgeon to perform a surgical procedure at the surgical site. In particular, the invention relates to an apparatus for stabilizing a predetermined area of the heart for performing minimally invasive coronary artery bypass grafting at the surgical site, in which the apparatus is adapted to be connected to a rib retractor, has a rotatable and pivotal joint between the handle and stabilizing device, and has a means for easily switching among different sized stabilizing devices.

2. Background Art

Atherosclerosis or coronary artery disease is among the most common and serious health problems confronting the medical profession. In the past, many different approaches at therapy have been utilized. Surgical correction of occluded or stenosed coronary arteries via bypass grafting through conventional approaches, such as the sternotomy, are probably still the most common procedure performed today, especially where multiple bypass grafts are needed.

However, interventional techniques, such as percutaneous transluminal angioplasty (PTCA), have gained popularity as the method of choice for therapy of atherosclerotic occlusions for several reasons. The transluminal approach is a minimally invasive technique which subjects the patient to less trauma and less recovery time, especially when compared to bypass grafts which utilize homologous tissue, such as saphenous vein grafts. Often the patient suffers complications at the graft donor site which are worse than the sternotomy and anastomosis.

Although PTCA procedures are often successful, complications such as restenosis or thrombosis and embolism can occur. Intravascular stents are sometimes deployed at the PTCA site to lessen the occurrence of restenosis. However, restenosed vessels often require surgical intervention for correction.

Surgical correction of restenosis, as well as conventional bypass graft surgery, require that the heart be stopped and the patient placed on a heart/lung bypass machine during the procedure. This occurs at considerable expense and risk to the patient. In an effort to reduce the expense, risk and trauma to the patient, physicians have recently turned to minimally invasive surgical approaches to the heart, such as intercostal and endoscopic access to the surgical site. In addition, utilization of alternative graft vessels, such as the internal mammary artery (IMA), have also greatly reduced the trauma to the patient and increased the efficacy of surgical therapy.

Prior to the present invention, however, attempts at performing minimally invasive bypass grafting on a beating heart were thought to be too tedious, dangerous and difficult because of the delicate nature of the surgical procedure, the lack of adequate access through a reduced surgical field, and the lack of a way to adequately stabilize and reduce movement at the graft site. Such a minimally invasive bypass grafting performed on the beating heart eliminates the expense and risk of stopping the heart and the necessity of the heart lung bypass machine and decreases patient recovery time. For single or double bypass procedures, especially where the IMA is utilized, patient trauma and recovery time is even further decreased.

SUMMARY OF THE INVENTION

The above problems of the prior art are overcome by the present invention, which provides an apparatus for stabilizing a predetermined area on a heart or other organ of a patient to enable a surgical procedure to be performed. The apparatus of the present invention comprises a bifurcated member having two prongs, an elongated handle segment, and a means for pivotally connecting the handle segment to the bifurcated member. Each prong of the bifurcated member, also known as a tine assembly, has a first section and a second section. The first section is adjacent the handle segment and terminates in the second section. The second section engages the heart or other organ on which the surgical procedure occurs.

The present invention also encompasses a means for movably mounting the handle segment to a rib retractor or other surgical device. The mounting means, which is preferably a swivel head, holds the bifurcated member at the predetermined site, thus alleviating the requirement that a person hold the handle segment.

A further aspect of the present invention is that it includes a means for rotatably and pivotally connecting the bifurcated member to the handle segment. In the preferred embodiment, a ball and socket design is used. In conjunction, the present invention comprises a means for locking the bifurcated member in a desired position relative to the handle segment when the bifurcated member is disposed on the heart of a patient. The surgeon can tighten the ball and socket to frictionally hold the assembly using a tightener located at the upper end of the handle segment, which is advantageous during a surgical procedure where space within the surgical site is limited.

Since the second section of the bifurcated member engages the heart, it is desired that the second section further comprises a means for stabilizing it from sliding on the heart. Stabilizing the apparatus on the heart is an important consideration during the surgical procedure. The present invention can encompass many different stabilizing means, including, for example, a DeBakey serrated pattern, a textured portion on at least a portion of one second section, an insert disposed on the second section having a plurality of teeth, an insert having a plurality of flexible hooks, an insert having a plurality of bristles, or even a flexible covering disposed over at least a portion of the second section. The flexible covering can be a cloth, such as cotton, or a tubular member formed from a material such as silicon.

As will be appreciated, the apparatus of the present invention can be used in surgical procedures other than heart surgery, including, for example, soft tissue procedures such as vascular thrombosis repair, intestinal resection and anastomosis and other intra-abdominal procedures, and the like.

Thus, it is an object of the invention to provide an apparatus for stabilizing a predetermined area of the heart or other organ of a patient to enable a surgeon to perform a surgical procedure at the predetermined site.

Another object of the invention is to provide an apparatus for stabilization of an area of the beating heart adjacent to a coronary artery for performing coronary artery bypass grafting.

Yet another objective of the present invention is to provide an apparatus in which the bifurcated member can both rotate and pivot relative to the handle segment to ensure the maximum adaptability for work within the surgical site. An associated objective is to use an apparatus in which the bifurcated member can be easily exchanged with another bifurcated member of a different size when necessary.

A further object of the invention is to provide an apparatus as above that is adapted for pivotal attachment to a device that provides access to the surgical site, such as a rib spreader or other retractor.

The above recited objects of the invention are not intended to so limit the used of the invention. These and other objects of the invention will be apparent to the skilled artisan based upon the following disclosure.

BRIEF DESCRIPTION OF THE FIGURES OF THE DRAWINGS

FIG. 5A is a front view showing the withdrawn position, in which the bifurcated member is spaced apart from the handle segment. FIG. 5B is a side view showing the ball being inserted into a section of the bore within the handle segment. FIG. 5C is a front view showing the occupied position, in which the ball is placed within the bore. FIG. 5D is a front view showing the engaged position, in which the socket engages the ball.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a" can mean one or more, depending upon the context in which it is used.

The present invention, as shown in FIGS. 1–8, encompasses an apparatus 10 for stabilizing a predetermined area on a heart of a patient to enable a surgical procedure to be performed. The apparatus 10, or stabilizer, comprises a bifurcated member 30 that is pivotally connected to an elongated handle segment 50. The handle segment 50 is preferably movably mounted to a rib spreader 20 or other similar equipment that remains stationary positioned on or adjacent to the patient during a surgical procedure.

Figure 1:
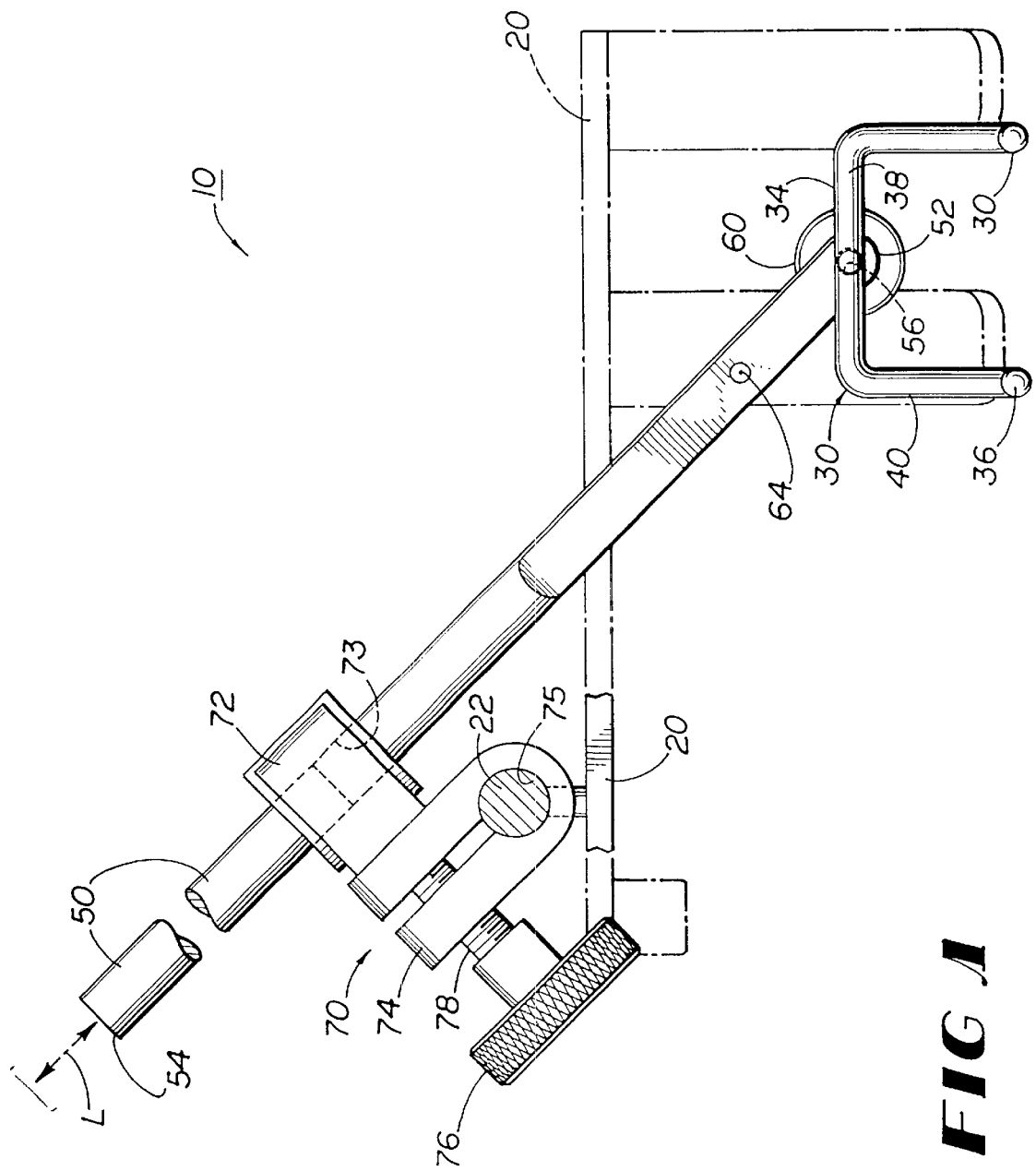
FIG. 1 is a side view of one embodiment of the present invention showing the stabilizer mounted to a rib retractor in which the bifurcated member is pivotally connected to the handle segment.
Figure 2:
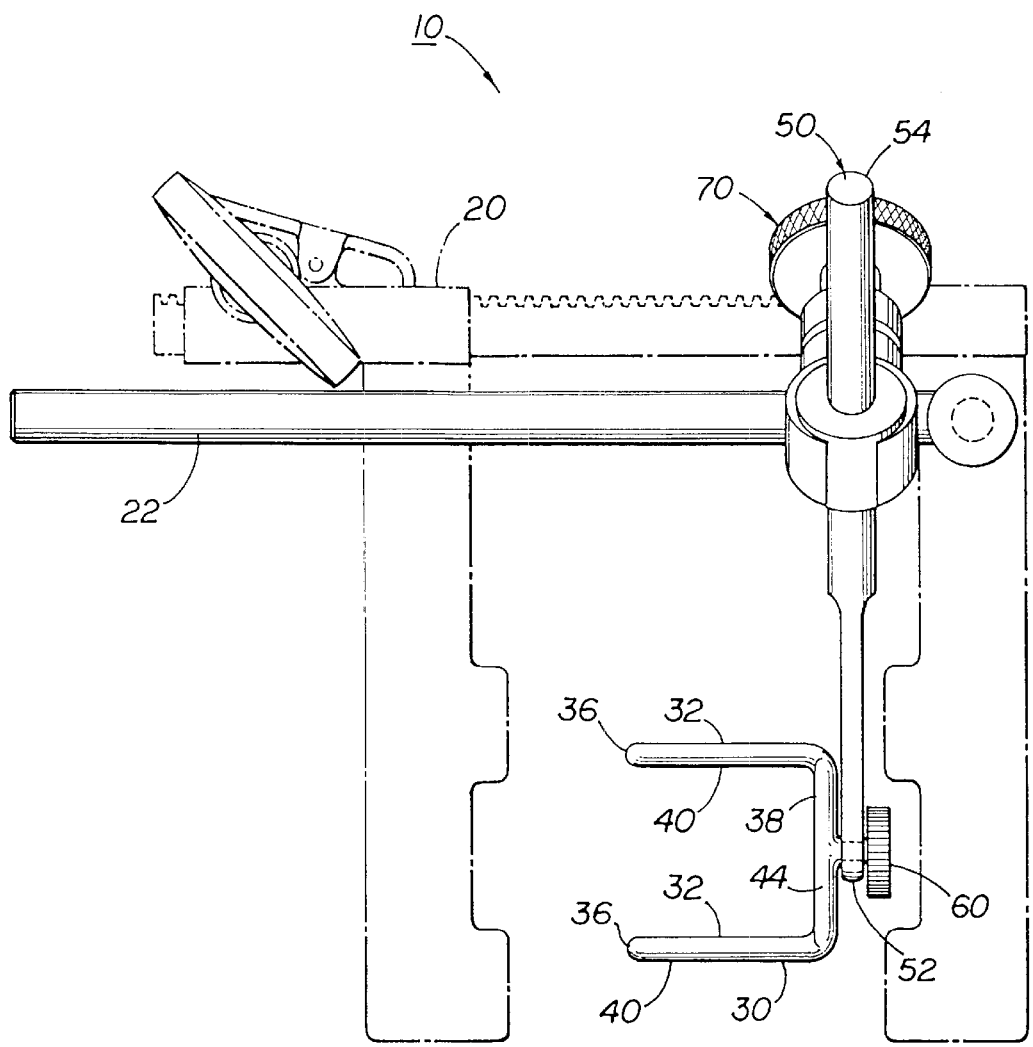
FIG. 2 is a top plan view of FIG. 1.

The present invention is ideal for use in heart surgery, in either conventional open heart surgery or by minimally invasive surgery, e.g., minimally invasive coronary artery bypass grafting. For minimally invasive surgery, access to the heart may be achieved through the ribs of the patient using a rib spreader 20, as shown in FIGS. 1 and 2. In the typical procedure, the surgeons will access the heart via the fourth intercostal space located between the third and fourth ribs, but this may be changed based on the individual patient's anatomy. Since, for the above reasons, this procedure is sometimes performed on a beating heart, it is advantageous to stabilize the heart in the area that the surgical procedure will occur.

When the present invention engages the surface of the heart, the surgeon applies a slight compressive force on the heart with the apparatus 10 in the area that the surgical procedure will occur so that the heart's movement at that specific area is diminished and stabilized. Stabilizing the heart is particularly useful for a heart suturing technique in the area of the coronary arteries such as the anastomosis of a bypass graft. In particular, it is advantageous to place a traction suture around an artery using a needle and suture thread while the present invention is stabilizing the surface of the heart adjacent to the artery. One skilled in the art will appreciate that the present invention, although ideal for heart surgery, can be used at any location on or within the body where tissue stabilization or isolation of a predetermined area is desired, including but not limited to the liver, kidneys, bladder, stomach, intestines, and vascular and other soft tissue surgery.

The bifurcated member 30 of the present invention has two elongated prongs 32 in which each prong 32 has a proximal end 34 and an opposite distal end 36 and each prong 32 forms a first section 38 and a second section 40. The prongs 32 are attached to each other adjacent their proximal ends 34. The first section 38 of each prong 32 is adjacent the proximal end 34 and terminates in the second section 40, and the second section 40 is adjacent the distal end 36. The second section 40 is adapted to engage a predetermined area on the heart or other organ of the patient.

Figures 6, 7, 8:
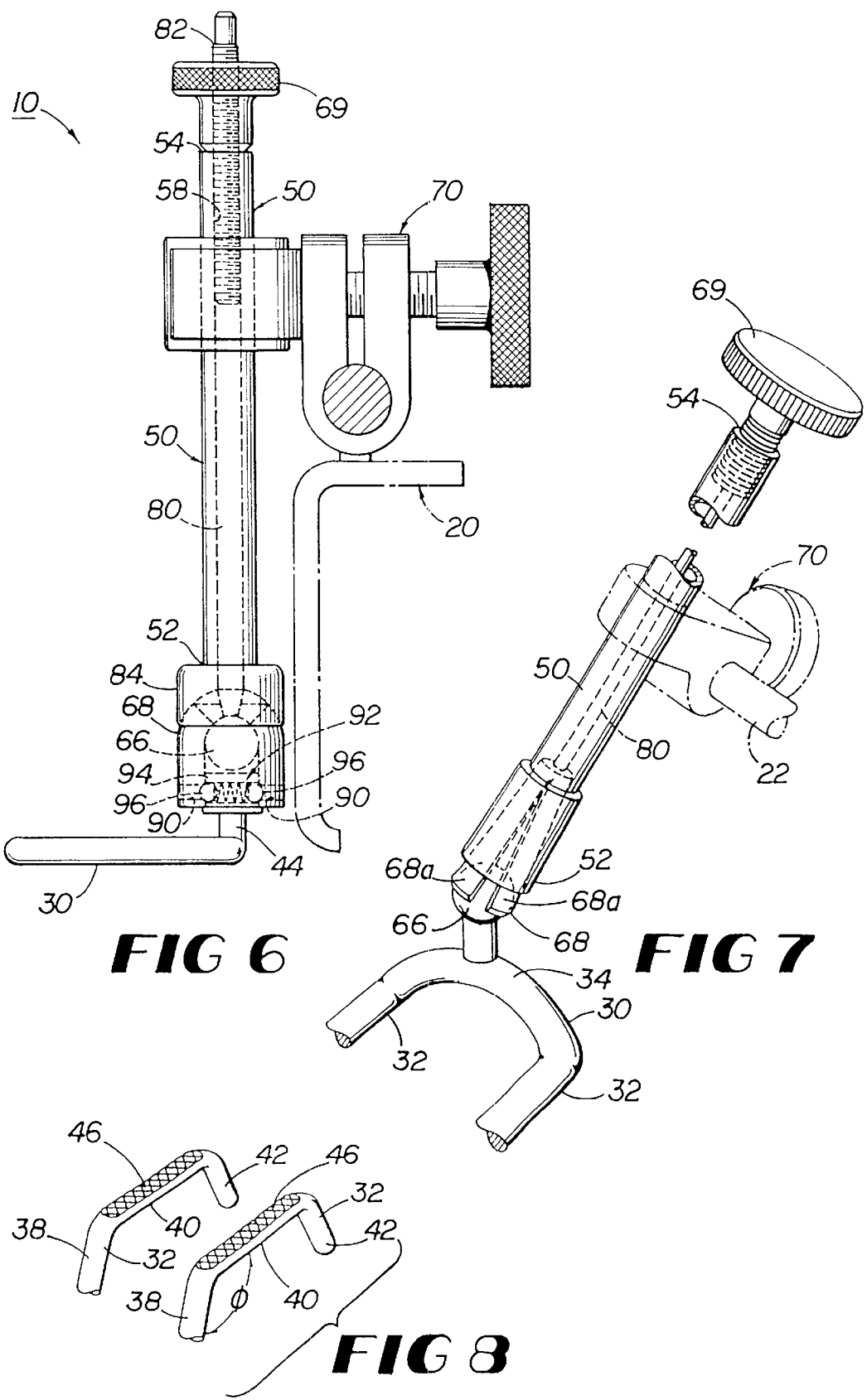
FIG. 6 is a side cross-sectional view of a second alternative embodiment of the stabilizer having a ball and socket pivotal and rotatable connecting means in which the bifurcated member is removable.
FIG. 7 is a perspective view of a third alternative embodiment of the stabilizer of the present invention having a ball and socket pivotal and rotatable connecting means.
FIG. 8 is a bottom perspective view of a portion of the bifurcated member of the present invention showing the textured surface on the second section of the prongs.

A third section 42, shown in FIG. 8, can be added to at least one of the prongs 32 at the end of the second section 40 that is opposite the first section 38. The third section 42 can be used as a tissue retractor or a retractor to pull a selected item, such as surgical thread, away from the area that the surgical procedure is being performed. In addition, the third section 42 can be advantageously positioned to secure surgical thread to a cleat (not shown) disposed on the handle segment 50.

Figure 3:
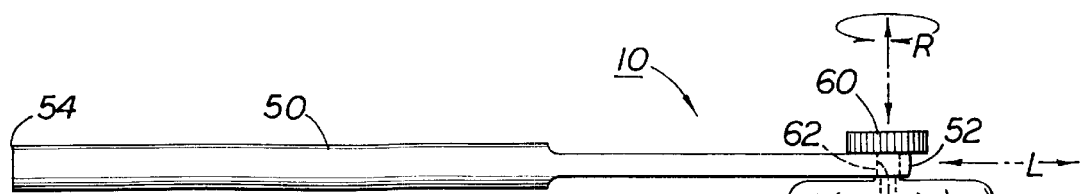
FIG. 3 is a side view of the stabilizer shown in FIG. 1.

As best shown in FIG. 3, a connecting member 44 is disposed intermediate the proximal end 34 of each prong 32, instead of directly connecting the prongs 32 to each other. The connecting member 44 has opposed ends in which each end is attached to the proximal end 34 of a respective prong 32. As one skilled in the art will appreciate, the length of the first section 38 can be very short so that the connecting member 44 would be either attached directly to or slightly separated from the second section 40. However, this alternate embodiment is not desirable because a separation height of at least a quarter (¼) of an inch is desired between the surface of the heart and the connecting member 44, to which the attached handle segment 50 is attached.

The handle segment 50 is used to extend the bifurcated member 30 into the chest of the patient to reach the surface of the heart. The handle segment 50 has a first end 52 and an opposite second end 54. The handle segment 50 also has an outer surface or member and a longitudinal axis L and defining a bore 56 therethrough. The bore 56 is disposed adjacent the first end 52 of the handle segment 50 and extends substantially perpendicular to its longitudinal axis L.

Referring now to FIGS. 1–4, the stabilizer 10 of the present invention comprises a means for pivotally connecting the first end 52 of the handle segment 50 to the two prongs 32 of the bifurcated member 30 adjacent their proximal ends 34. The pivotal connecting means comprises a positioning member 60 and a rod 62 rotatably disposed through the bore 56 in the handle segment 50. The rod 62 has opposed ends and a length extending therebetween. One end of the rod 62 is fixedly attached to the positioning member 60 and the opposed end of the rod 62 is fixedly attached to the connecting member 44 so that the bifurcated member 30 is at least partially rotatable about an axis of rotation R, which is parallel to and disposed through the bore 56 of the handle segment 50. Preferably, the length of the rod 62 is of a size to allow rotation of the bifurcated member 30 but to prevent transverse, or lateral, movement of the bifurcated member 30 relative to the longitudinal axis L of the handle segment 50. That is, the bifurcated member 30 is rotatable but does not have undesirable lateral play.

As shown in FIG. 1, the stabilizer 10 can use a pin 64 fixedly attached to a portion of the handle segment 50 intermediate its first and the second ends 52, 54. The pin 64 is disposed to block complete rotation of the bifurcated member 30 so that bifurcated member 30 is rotatable less than 360° about the bore 56 of the handle segment 50. This prevents the bifurcated member 30 flipping to an inverted position when the surgeon is placing the second section 40 of the prongs 32 on the heart of the patient.

The advantage of the pivotal connecting means is that the second sections 40 can be disposed at the predetermined location on the heart and the bifurcated member 30 disposed in the desired position relative to the handle segment 50, such as the handle segment 50 being oriented to a position that does not interfere with the surgeon performing the surgical procedure. That is, once the bifurcated member 30 is properly positioned, then the handle segment 50 is moveable to the desired position relative to the bifurcated member 30 and, optionally, locked at that position by a mechanical device, such as a swivel head, so that the handle segment 50 does not interfere with the surgery.

The connecting means can alternatively connect the handle segment 50 to the bifurcated member 30 so that the bifurcated member 30 is both rotatable and pivotal relative to the handle segment 50. The increased movement of a rotatable and pivotal connecting means is preferred compared with the pivotal connecting means shown in FIGS. 1–4.

Figure 5:
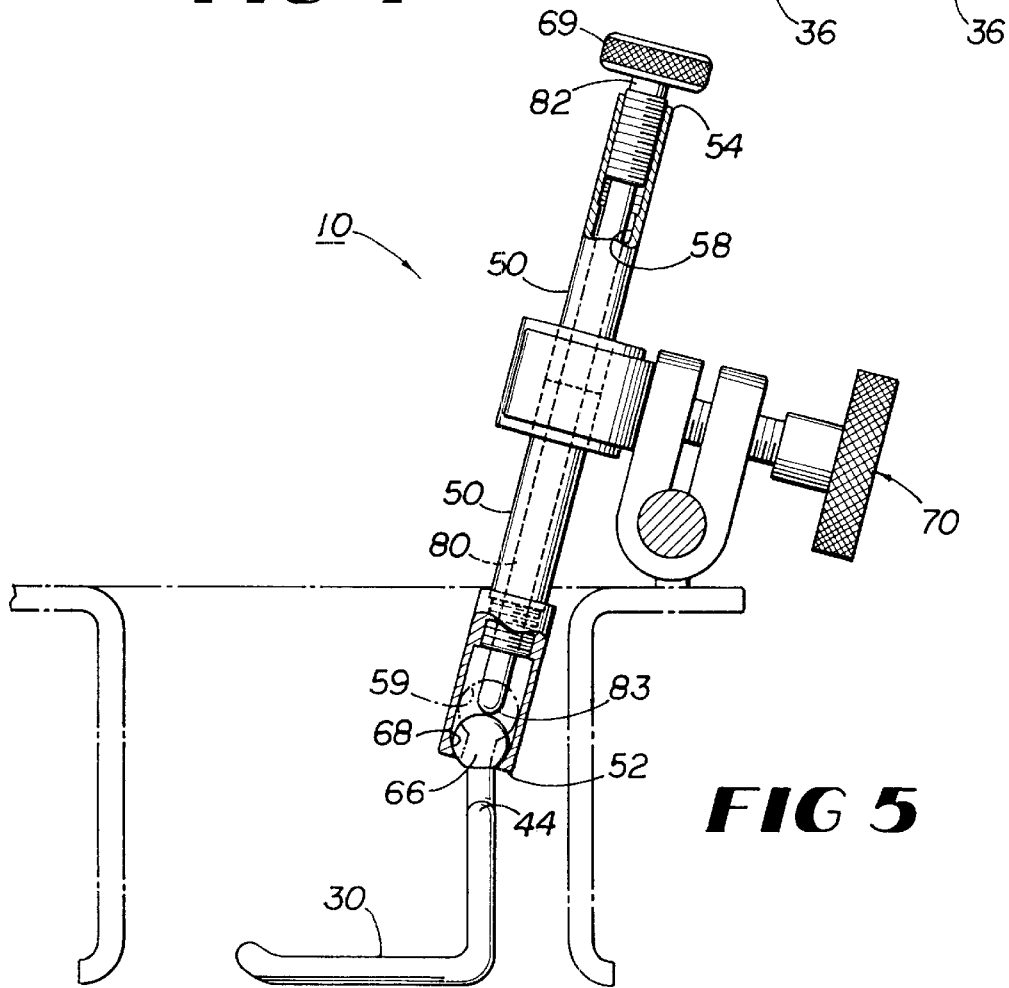
FIG. 5 is a side view, partially in cross section, of a first, preferred embodiment of the stabilizer having a ball and socket pivotal and rotatable connecting means in which the bifurcated member is removable.

Referring now to FIG. 5, a first, preferred embodiment of the connecting means is shown in which the bifurcated member 30 is rotatably and pivotally movable relative to the handle segment 50. The connecting means uses a ball and socket for connecting the first end 52 of the handle segment 50 to the bifurcated member 30 so that the bifurcated member 30 is movable to the desired position.

The connecting means comprises a longitudinally-extending bore 58 formed within at least a portion of the handle segment 50 and a ball 66 disposed within a portion of the bore 58. The ball 66 is placed adjacent the first end 52 of the handle segment 50 and a portion of the ball 66 is fixedly attached to the bifurcated member 30, preferably the connecting member 44. The ball 66 is movably secured within the bore 58, wherein the ball 66 and attached bifurcated member 30 are rotatably and pivotally movable relative to the handle segment 50 without separating therefrom.

This preferred embodiment of the connecting means further comprises a means for locking the connecting means so that the bifurcated member 30 is held in the desired position. The locking means preferably comprises a shaft 80 disposed, at least partially, within the bore 58, a socket 68 attached to the shaft 80, and a means for adjustably positioning the shaft 80 and attached socket 68 within the bore 58. The shaft 80 has an upper end 82 and an opposite lower end 83, to which the socket 68 is attached. The socket 68 can be integrally formed into the lower end 83 of the shaft 80 or, alternatively, a separate component attached to the shaft 80. The socket 68 has an interior surface of a size to complimentarily and detachably engage the ball 66. Preferably, the socket 68 forms a 180° arc in cross section to provide the maximum surface area to contact the ball 66.

The adjustable positioning means moves the shaft 80 and attached socket 68 within the bore 58 between an engaged position and a disengaged position. In the engaged position, the interior surface of the socket 68 detachably engages the ball 66 to frictionally hold the ball 66 in the desired position, which is preferably set after the bifurcated member 30 is disposed on the heart and the attached handle segment 50 oriented to the desired position. In the disengaged position, the interior surface of the socket 68 and the ball 66 are spaced apart so that the ball 66 and attached bifurcated member 30 are movable. Of course, the interior surface of the socket 68 and ball 66 do not need to be completely spaced apart to be in the disengaged position, but, instead, sufficiently separated to allow movement therebetween. That is, in the disengaged position, the socket 68 and ball 66 are adequately physically separated, or disengaged, so that the socket 68 does not frictionally hold or lock the ball 66 in a non-movable position.

Preferably, the positioning means also comprises a portion of the bore 58 complementarily engaging a portion of the shaft 80. The interface between the bore 58 and shaft 80 controls the relative movement therebetween as the shaft 80 is moved within the bore 58. It is preferred that the portions of the bore 58 and the shaft 80 that engage each other are complementarily threaded surfaces, although other embodiments may be used, such as a protrusion (not shown) on the shaft 80 that traverses along a channel (not shown) in the bore 58 to maintain the desired relative longitudinal position therebetween. As shown in FIG. 5, the bore 58 has a length extending between the first and second ends 52, 54 of the handle segment 50 and the length of the shaft 80 is about the same as the length of the bore 58. A tightener 69 is fixedly attached to the upper end 82 of the shaft 80 and disposed outside the bore 58. Rotation of the tightener 69 causes the attached shaft 80 and socket 68 to move longitudinally between the engaged and disengaged positions because of the complementarily threaded surfaces of the shaft 80 and bore 58 engaging each other.

FIG. 6 shows a second embodiment of the rotatable and pivotal connecting means, which also uses a ball and socket. This embodiment comprises the bore 58 longitudinally extending through the handle segment 50 and the shaft 80 being disposed within the bore 58. The ball 66 is fixedly attached to the lower end 83 of the shaft 80. The socket 68 has an interior surface, a top end, and an opposed bottom end, which is adapted to mount the bifurcated member 30 thereto. The interior surface of the socket 68 complementarily and detachably engages the ball 66. The socket 68 also defines an opening therein adjacent its top end through which a portion of the shaft 80 extends. A bowl-shaped member 84 is fixedly attached to the first end 52 of the handle segment 50 for receiving a portion of the socket 68 therein.

Similar to the first ball and socket embodiment, this embodiment of the connecting means also comprises a means for locking the connecting means so that the bifurcated member 30 is held in the desired position. In the engaged position, the interior surface of the socket 68 engages the ball 66 and the bowl-shaped member 84 engages the opposite surface of the socket 68 so that the bowl-shaped member 84 and the ball 66 frictionally hold the socket 68 disposed therebetween in the desired position. In the disengaged position, the socket 68 and the bowl-shaped member 84 are spaced apart so that the socket 68 and attached bifurcated member 30 are movable. Similar to the first ball and socket embodiment discussed above, the components do not need to be completely spaced apart in the disengaged position, but sufficiently separated so that the ball 66 and bowl-shaped member 84 do not prevent the socket 68 and attached bifurcated member 30 from moving.

Also, similar to the first ball and socket embodiment, the positioning means preferably comprises a threaded portion of the bore 58 complementarily engaging a threaded portion of the shaft 80. However, unlike the first ball and socket embodiment, the tightener 69 is rotatably attached to the second end 54 of the handle segment 50 instead of being fixedly attached to the shaft 80. The tightener 69 defines a threaded bore therethrough which complementarily engages a section of the threaded portion of the shaft 80 so that rotations of the tightener 69 longitudinally moves the shaft 80 between the engaged and disengaged positions. When the surgeon tightens the tightener 69, the ball 66 is moved toward the handle segment 50, which correspondingly moves the socket 68 into the bowl-shaped member 84. The surgeon continues to turn the tightener 69 until the socket 68 is securably seated in the bowl-shaped member 84 with the bifurcated member 30 at a desired orientation. As shown in FIG. 6, the socket 68 allows the shaft 80 to be pivoted thirty degrees (30°) in all directions relative to its centerline, but can be designed pivot up to ninety degrees (90°).

FIG. 7 shows a third ball and socket embodiment of the connecting means which comprises a socket 68 disposed at the first end 52 of the handle segment 50 and a ball 66 joined to the bifurcated member 30. The ball 66 is complementarily received within the socket 68. Preferably, the connecting means also comprises a means for locking the ball 66 in the desired position. Here, the socket 68 is formed of a plurality of individual segments 68a that can be pulled toward each other to lock, or frictionally hold, the ball 66 in the desired position. To pull the segments 68a together, the tightener 69 is rotated, which moves the shaft 80 disposed through the bore 58. The shaft 80 interconnects the socket 68 with the tightener 69 and when the shaft 80 pulls the socket 68 toward the tightener 69 and a portion of the socket 68 into the first end 52 of the handle segment 50, the handle segment 50 constricts the size of the socket 68. Constriction of the socket 68 causes the segments 68a to be pulled together and securely hold the ball 66.

Other connecting means are contemplated including, for example, a hinged connection (not shown) in which the handle segment 50 only pivots in a plane other than the plane shown in FIGS. 1–4. Another possible embodiment is a swivel mechanism (not shown), similar to a swivel used in fishing. However, as one skilled in the art will appreciate, it is preferred to use a connecting means that both rotatably and pivotally connects the bifurcated member 30 to the handle segment 50 and that can lock the bifurcated member 30 when disposed on the heart in a desired position relative to the handle segment 50.

The connecting means can further comprise a means for removably, or interchangeably, mounting the bifurcated member 30 to the handle segment 50. The bifurcated member 30 thus can be detachably secured to the handle segment 50 and is interchangeable with another bifurcated member 30, e.g., a bifurcated member in which the prongs are a different size or have a different separation distance therebetween.

Figure 5A:
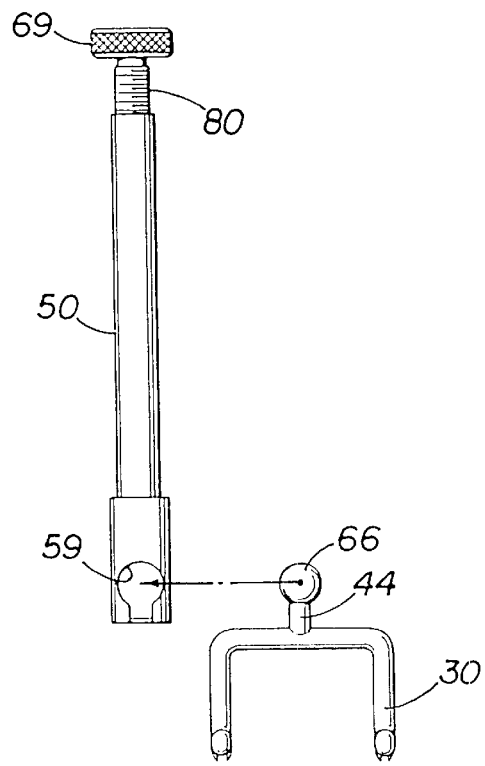
FIGS. 5A–5D are views of FIG. 5 showing the bifurcated member being attached to the handle segment and then being locked in the desired position.
Figure 5B:
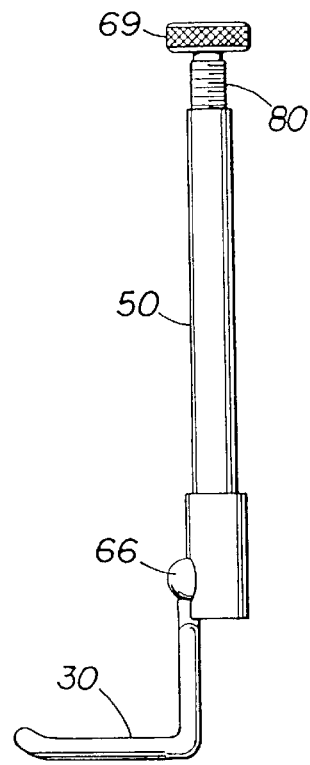
Figure 5C:
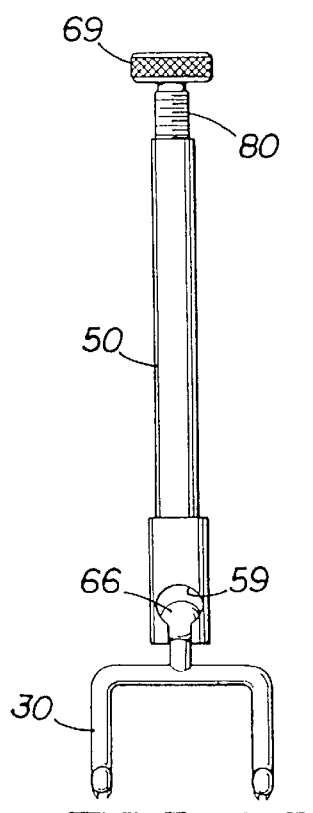
Figure 5D:
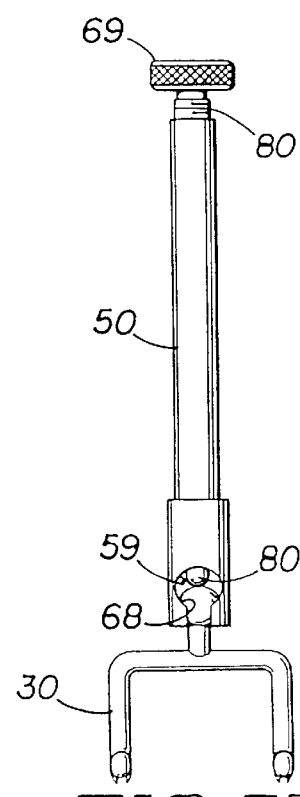

For the preferred embodiment shown in FIGS. 5 and 5A–5D, the removable mounting means comprises a portion of the handle segment 50 defining an opening 59 therethrough. The opening 59 is of a size through which the ball 66 can traverse so that the ball 66 is movable between an occupied position and a withdrawn position. In the withdrawn position, the ball 66 is removed from the bore 58, as shown in FIG. 5A. FIG. 5B shows the ball 66 being placed into the bore 58 through the opening 59. In the occupied position, the ball 66 is disposed within the bore 58, which is shown in FIG. 5C. FIG. 5D show the shaft 80 moved toward the first end 52 of the handle segment 50 so that the socket 68 engages the ball 66.

The opening 59 in the handle segment 50 is disposed intermediate the first and second ends 52, 54 of the handle segment 50. Once the ball 66 traverses through the opening 59 and enters into the bore 58, as shown in FIG. 5B, the ball 66 is moved toward the first end 52 of the handle segment 50, as shown in FIGS. 5C and 5D, where it cannot be laterally moved and withdrawn through the opening 59. That is, the ball 66 must be moved upward toward the second end of the handle segment 50 to be realigned with the opening 59 to be removed from the bore 58. Thus, when the shaft 80 and attached socket 68 are in the engaged position, as shown in FIG. 5D, the ball 66 and attached bifurcated member 30 are prevented from moving to the withdrawn position.

Referring again to FIG. 6, the removable mounting means of the second embodiment comprises a detent 90 formed in the interior side of the socket 68 adjacent its bottom end. The connecting member 44 is attached to a plunger device 92 that has a shell 94 containing at least one circular member 96 and a means for biasing the circular member 96 away from the center of the shell 94. An example of the biasing means is a spring (not shown).

The shell 94 has an outer periphery that is complementarily received within a portion of the interior surface of the socket 68 adjacent its bottom end when no portion of the circular member 96 extends outwardly from the shell 94. The biasing means, however, biases a portion of the circular member 96 to extend past the outer periphery of the shell 94. When the shell 94 is pushed into the socket 68, the normally outwardly-projecting circular member 96 is forced toward the center of the shell 94 against the opposing force of the biasing means. Once the shell 94 is pushed far enough into the socket 68 so that the circular member 96 aligns with the detent 90, the biasing means forces the circular member 96 into the detent 90, as shown in FIG. 6. The shell 94 remains detachably secured in this position until a force is applied to the shell 94, such as downwardly pulling on the bifurcated member 30, to overcome the force of the biasing means. Thus, the plunger device 92 is movable between an occupied position, in which a portion of the plunger device 92 is disposed within the socket 68, and a withdrawn position, in which the plunger device 92 is spaced apart from the socket 68. Thus, bifurcated members are interchangeable in the present invention, which is advantageous for different patients or changes in circumstances that arise during the surgical procedure.

In an alternate embodiment, the removable mounting means comprises the interior surface of the socket having a threaded surface (not shown) and a portion of the shell having a complementarily threaded surface (not shown) that detachably connects to the socket. However, this alternate embodiment is less desirable because it could allow rotation of the bifurcated member to occur.

The present invention preferably further comprises a means for movably mounting the handle segment 50 to a rib retractor 20. Referring back to FIGS. 1 and 2, it is preferred that the mounting means comprises a swivel head 70 having a first portion 72, a second portion 74, and a tightening portion 76. The first portion 72 defines a slot 73 therethrough which is of a size to slidably and adjustably receive a portion of the handle segment 50 therein. The handle segment 50, accordingly, is movable in the slot 73 longitudinally and rotationally relative to the first portion 72 of the swivel head 70.

The second portion 74 defines an opening 75 therethrough which is adapted to detachably and slidably engage a portion of the rib retractor 20, preferably, an elongated slide segment 22. That is, the second section 40 allows movement of the handle segment 50 and attached bifurcated member 30 in all directions relative to the slide segment 22. The second section 40 is slidable along the slide segment 22 and is pivotal transversely relative to the slide segment 22. Furthermore, the handle segment 50 is rotatable so that its longitudinal axis L can form different angles relative to the length, or longitudinal axis, of the slide segment 22. The handle segment 50 thus is movable to any position except where the swivel head 70, handle segment 50, or bifurcated member 30 are blocked by an obstruction, such as a portion of the rib retractor 20. This freedom of movement, coupled with the movement that the pivotal connecting means and first portion 72 provides, allow the surgeon the greatest flexibility to dispose the second section 40 of each prong 32 on the heart while the handle segment 50 is movably connected to the rib retractor 20.

An advantage of the present invention is that the handle segment 50 and bifurcated member 30 can be pre-aligned so that the bifurcated member 30 is self-positioning on the patient's heart by lowering the handle segment 50. Once the surgeon lowers the bifurcated member 30 to the desired position, the surgeon can then maintain the second sections 40 engaging the heart while re-orienting the handle segment 50, if required, to a position that allows the greatest access to the surgery site. When the handle segment 50 is at the desired orientation, the tightening portion 76 of the swivel head 70 is tightened, preferably by a single turn of the tightening portion 76, to secure the handle segment 50 at a desired position.

The tightening portion 76 operates by a screw member 78 disposed through a section of the swivel head 70 tightening the first and second portions 72, 74 in place. Thus, the tightening portion 76 detachably secures the handle segment 50 at a desired orientation in the slot 73 of the first portion 72 and the swivel head 70 at a desired position on the rib retractor 20 so that the surgeon is free to perform the surgical procedure. The tightened portion can be easily loosened, when desired, to allow the handle segment 50 and the bifurcated member 30 to be moved.

The handle segment 50 thus is held in the desired position by a connection with the rib retractor 20 that is necessary to preform the surgical procedure. As shown best in FIG. 2, the stabilizer 10 can be disposed to the side of the rib retractor 20 so that it allows a wide angle of access to the surgical site. An undesirable alternative is to have another surgeon or nurse hold the handle segment 50 during the surgical procedure, which creates problems with space constraints, fluctuations in the pressure of the second sections 40 on the heart, and increased costs for the extra person to hold the handle segment 50.

As one skilled in the art will appreciate, there are numerous other options available to mount the handle segment 50 to the rib retractor 20 or other surgical equipment so that the second section 40 is maintained at a desired position without a person physically holding the apparatus 10. One example of such a mounting means is a ball and socket connection (not shown). However, it has been found that the swivel head is a more desirable mounting means because of the control and ease of locking the bifurcated member 30 and handle segment 50 at the desired position.

Figure 4:
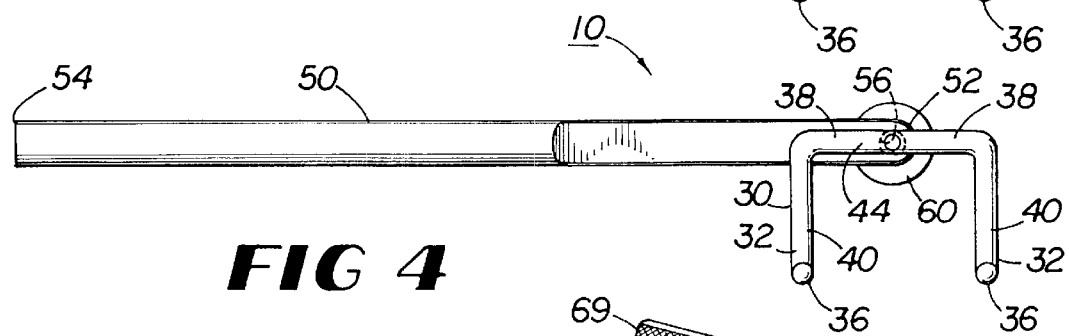
FIG. 4 is a bottom plan view of FIG. 3.

Referring now to FIGS. 3 and 4, the second section 40 each of the two prongs 32 is preferably disposed substantially perpendicular to the longitudinal axis L of the handle segment 50, regardless of the direction that the bifurcated member 30 pivots. It is also preferred that the second sections 40 of each of the two prongs 32 are co-planar and that the juncture between the first section 38 and the second section 40 of the prongs 32 of the bifurcated member 30 form an approximately 90°, or right, angle φ therebetween, as shown in FIG. 8. A right, or even obtuse, angle φ is preferred so that the surgeon has better access to the area that the surgical procedure is performed. An acute angle could be used, but it is less desirable because it would likely interfere with the surgical procedure.

For use in heart surgery, the apparatus 10 has certain size limitations. For example, the available area to a surgeon to perform a minimally invasive surgical procedure on the heart via an intercostal approach is approximately three (3) inches by one and a half (1½) inches, which, of course, may vary between patients. Accordingly, it is desired that the width between the second sections 40 be in the range of one half (½) to one and a quarter (1¼) inches, more preferably in the range of three quarters (¾) of an inch to one (1) inch. These widths are narrow enough to fit into the confined space, yet wide enough to bridge the area of interest, e.g., bridge an artery that is to be bypassed.

In a preferred embodiment, the length of the second section 40 is in the range of one half (½) inch to one and a half (1½) inches, more preferably in the range of two-thirds (⅔) of an inch to three quarters (¾) of an inch. In the preferred embodiment, each second section 40 is one (1) inch long and separated by three quarters (¾) of an inch to one (1) inch from the other second section 40.

Since the second section 40 engages the heart, it is preferable that this section further comprise a means for stabilizing the second section 40 from sliding on the heart when in contact therewith. That is, the stabilizing means resists sliding or slipping motion between the surface of the heart and the second section 40. The stabilizing means increases the coefficient of friction but should not have a texture that may potentially damage tissue of the heart or other vital organs.

In one embodiment shown in FIG. 8, the stabilizing means comprises a textured surface 46 which is a knurled texture. Other embodiments are contemplated, such as a DeBakey serrated pattern (not shown) or a plurality of intersecting slits (not shown) that prevent the second section 40 from sliding when it engages the heart. As one skilled in the art will appreciate, other stabilizing means can be used so long as the stabilizing means atraumatically grips the tissue.

Another contemplated embodiment of the stabilizing means includes a removable insert (not shown) having an attaching surface secured to the second section 40 of each prong 32 and an opposite stabilizing surface (not shown) which carries the stabilizing means. The stabilizing surface of the insert can comprise a plurality of tungsten carbide or stainless steel teeth forming the DeBakey or other pattern. Another embodiment is that the stabilizing surface comprises a plurality of flexible hooks (not shown). The preferred hooks are those of a hook and loop fastener, commonly referred to as VELCRO® fasteners. Still another embodiment comprises a plurality of bristles (not shown) in which the bristles are disposed at a plurality of different orientations, similar to that of a tube or glass cleaner. Because of the multiple orientations of the bristles, any direction that the second section 40 tends to slide is resisted by bristles oriented that direction that contact the surface of the heart to resist the motion.

Yet another embodiment of the stabilizing means comprises a flexible covering disposed over at least a portion of the second section 40. The covering can be a cloth, such as cotton, braided cotton, linen or other coverings that resist motion when disposed on the surface of a heart. Similarly, the covering can be a tubular member selected from the group of silicon, rubber, or plastic as well as other materials that resist motion when disposed on the surface of a heart.

Although the present invention has been described with reference to specific details of certain embodiments thereof, it is not intended that such details should be regarded as limitations upon the scope of the invention except as and to the extent that they are included in the accompanying claims.

What is claimed is:

1. A stabilizer, comprising:
   a. a bifurcated member having two elongated prongs, each prong having a proximal end and an opposite distal end, said prongs attached to each other adjacent the proximal ends thereof, at least a portion of each prong adapted to engage a heart of a patient;
   b. an elongated handle segment having a first end and an opposite second end; and
   c. means for rotatably and pivotally connecting the first end of said handle segment to said bifurcated member, wherein said connecting means allows said bifurcated member to rotate and pivot relative to said handle segment so that said bifurcated member is movable to a desired position, wherein said connecting means comprises:
      i. a longitudinally-extending bore within said handle segment; and
      ii. a ball, said ball disposed within said bore adjacent the first end of said handle segment, a portion of said ball fixedly attached to said bifurcated member, said ball movably secured within said bore so that said ball and attached bifurcated member are rotatably and pivotally movable relative to said handle segment; and
   d. means for locking said connecting means so that said bifurcated member is held in the desired position, wherein said locking means comprises:
      i. a shaft having an upper end and an opposite lower end, at least a portion of said shaft complementarily received within said bore;
      ii. a socket attached to the lower end of said shaft, said socket having an interior surface of a size to complementarily and detachably engage said ball; and
      iii. means for adjustably positioning said shaft and attached socket within said bore between an engaged position, in which the interior surface of said socket detachably engages said ball to frictionally hold said ball in the desired position, and a disengaged position, in which the interior surface of said socket and said ball are spaced apart so that said ball is removable from said handle segment.

2. The stabilizer of claim 1, wherein said positioning means further comprises a portion of said bore complementarily engaging a portion of said shaft so that the interface therebetween controls the relative movement between said shaft and said bore as said shaft is moved within said bore.

3. The stabilizer of claim 2, wherein the portions of said bore and said shaft that engage each other are complementarily threaded surfaces.

4. The stabilizer of claim 3, wherein said bore extends between the first and second ends of said handle segment, said bore having a length, wherein a portion of said shaft extends substantially the length of said bore, and wherein said shaft further comprises a tightener fixedly attached to the upper end thereof and disposed outside said bore, wherein rotation of said tightener moves said shaft and socket longitudinally between the engaged and disengaged positions.

5. The stabilizer of claim 1, wherein said shaft and said socket are integral.

6. A stabilizer, comprising:
   a. a bifurcated member having two elongated prongs, each prong having a proximal end and an opposite distal end, said prongs attached to each other adjacent the proximal ends thereof, at least a portion of each prong adapted to engage a heart of a patient;
   b. an elongated handle segment having a first end and an opposite second end; and
   c. means for rotatably and pivotally connecting the first end of said handle segment to said bifurcated member, wherein said connecting means allows said bifurcated member to rotate and pivot relative to said handle segment so that said bifurcated member is movable to a desired position, wherein said connecting means comprises:
      i. a longitudinally-extending bore within said handle segment; and
      ii. a ball, said ball disposed within said bore adjacent the first end of said handle segment, a portion of said ball fixedly attached to said bifurcated member, said ball movably secured within said bore so that said ball and attached bifurcated member are rotatably and pivotally movable relative to said handle segment without separating therefrom; and
   wherein said connecting means further comprises means for removably mounting said bifurcated member to said handle segment, and wherein said removable mounting means comprises a portion of said handle segment defining an opening therethrough for allowing said ball to traverse therethrough so that said ball is movable between a occupied position, in which said ball is disposed within said bore, and a withdrawn position, in which said ball is removed from said bore.

7. The stabilizer of claim 6, wherein the opening of said handle segment is disposed intermediate the first and second ends of said handle segment and wherein, when said shaft and attached socket are in the engaged position, said ball is positioned closer to the first end of said handle segment than when said ball traverses through the opening, whereby said ball and attached bifurcated member are prevented from moving to the withdrawn position.

8. A stabilizer, comprising:
 a. a bifurcated member having two elongated prongs, each prong having a proximal end and an opposite distal end, said prongs attached to each other adjacent the proximal ends thereof, at least a portion of each prong adapted to engage a heart of a patient;
 b. an elongated handle segment having a first end and an opposite second end; and
 c. means for rotatably and pivotally connecting the first end of said handle segment to said bifurcated member, wherein said connecting means allows said bifurcated member to rotate and pivot relative to said handle segment so that said bifurcated member is movable to a desired position, wherein said connecting means comprises:
  i. a bore longitudinally extending through said handle segment;
  ii. a shaft having an upper end and an opposite lower end, at least a portion of said shaft complementarily received within said bore;
  iii. a ball fixedly attached to the lower end of said shaft;
  iv. a socket having an interior surface, a top end and an opposed bottom end, wherein said interior surface complementarily and detachably engages said ball, said socket defining an opening therein adjacent the top end thereof through which a portion of said shaft adjacent said ball extends, the bottom end of said socket adapted to mount said bifurcated member thereto; and
  v. a bowl-shaped member fixedly attached to the first end of said handle segment for receiving a portion of said socket therein.

9. The stabilizer of claim 8, further comprising means for locking said connecting means so that said bifurcated member is held in the desired position.

10. The stabilizer of claim 9, wherein said locking means comprises means for adjustably positioning said shaft relative to said handle segment between an engaged position, in which the interior surface of said socket engages said ball and said bowl-shaped member engages said socket so that said bowl-shaped member and said ball frictionally hold said socket disposed therebetween in the desired position, and a disengaged position, in which said socket and said bowl-shaped member are spaced apart so that said socket and attached bifurcated member are movable.

11. The stabilizer of claim 10, wherein said positioning means further comprises a portion of said bore complementarily engaging a portion of said shaft so that the interface therebetween controls the relative movement between said shaft and said bore as said shaft is moved within said bore.

12. The stabilizer of claim 11, wherein the portions of said bore and said shaft that engage each other are complementarily threaded surfaces.

13. The stabilizer of claim 12, wherein said bore extends between the first and second ends thereof, said bore having a length, wherein a portion of said shaft extends substantially the length of said bore, and wherein said handle segment further comprises a tightener rotatably attached to the second end thereof, wherein said tightener defines a threaded bore therethrough which complementarily engages a section of the threaded portion of said shaft, wherein rotation of said tightener longitudinally moves said shaft between the engaged and disengaged positions.

14. The stabilizer of claim 13, wherein said connecting means further comprises means for removably mounting said bifurcated member to said socket.

15. The stabilizer of claim 14, wherein said removable mounting means comprises:
 a. a detent in the interior surface of said socket;
 b. a plunger device having a shell and at least one circular member disposed within said shell, the shell having a center and an outer periphery, the outer periphery complementarily received within a portion of the interior surface of said socket; and
 c. means for biasing the circular member of said plunger device away from the center of the shell toward its outer periphery so that a portion of said circular member is biased to extend past the outer periphery,
 wherein said plunger device is movable between an occupied position, in which a portion of said plunger device is disposed within the interior surface of said circular member so that a portion of said circular member is disposed within the detent of said socket, and a withdrawn position, in which said plunger device is spaced apart from said socket, and
 wherein, when in the occupied position, said biasing means biases said circular member into the detent of said socket preventing said bifurcated member from freely separating from said socket.

16. A stabilizer, comprising:
 a. a bifurcated member having two elongated prongs, each prong having a proximal end and an opposite distal end, said prongs attached to each other adjacent the proximal ends thereof, at least a portion of each prong adapted to engage a heart of a patient;
 b. an elongated handle segment having a first end and an opposite second end; and
 c. means for rotatable and pivotally connecting the first end of said handle segment to said bifurcated member, wherein said connecting means allows said bifurcated member to rotate and pivot relative to said handle segment so that said bifurcated member is movable to a desired position, wherein said connecting means comprises:
  i. a longitudinally-extending bore within said handle segment; and
  ii. a ball, said ball disposed within said bore adjacent the first end of said handle segment, a portion of said ball fixedly attached to said bifurcated member, said ball movably secured within said bore so that said ball and attached bifurcated member are rotatable and pivotally movable relative to said handle segment;
 d. means for locking said connecting means so that said bifurcated member is held in the desired position, wherein said locking means comprises:
  a. a shaft having an upper end and an opposite lower end, at least a portion of said shaft complementarily received within said bore;
  b. a socket attached to the lower end of said shaft, said socket having an interior surface of a size to complementarily and detachably engage said ball; and
  c. means for adjustably positioning said shaft and attached socket within said bore between an engaged position, in which the interior surface of said socket detachably engages said ball to frictionally hold said ball in the desired position, and a disengaged position, in which the interior surface of said socket and said ball are spaced apart so that said ball is removable from said handle segment.

17. An apparatus for stabilizing a predetermined area of a heart, the apparatus comprising:
   a. a stabilizing device having a first surface sized to contact the predetermined area of the heart of a patient and a second surface thereon;
   b. an elongated handle member having a first end and an opposite second end;
   c. a connecting member for rotatably and pivotally connecting said stabilizing device to said handle member, wherein said connecting member consists of a ball and socket member, where one of the ball member or said socket member is connected to the first end of the handle member and the other of the ball member or said socket member is connected to the second surface of the stabilizing member and wherein said ball member is removable from said socket member to enable said stabilizing device to be removed from said handle member; and
   d. wherein said socket member includes a sidewall having a slot therein and said slot is sized to receive said ball member therethrough.

18. An apparatus for stabilizing a predetermined area of a heart, the apparatus comprising:
   a. a stabilizing device having a first surface sized to contact the predetermined area of the heart of a patient and a second surface thereon;
   b. an elongated handle member having a first end and an opposite second end;
   c. a connecting member for rotatable and pivotally connecting said stabilizing device to said handle member, wherein said connecting member consists of a ball and socket member, where one of the ball member or said socket member is connected to the first end of the handle member and the other of the ball member or said socket member is connected to the second surface of the stabilizing member and wherein said ball member is removable from said socket member to enable said stabilizing device to be removed from said handle member; and
   d. wherein said handle member includes an outer member and longitudinally extending bore extending between said first and second ends thereof and a shaft extending through said bore, wherein said shaft and said outer member are movable with respect to each other to allow for the selective locking of the ball member in the socket member to prevent the rotatable movement of said stabilizing device with respect to said handle member.

19. An apparatus for stabilizing a predetermined area of a heart, the apparatus comprising:
   a. a stabilizing device having a first surface sized to contact the predetermined area of the heart of a patient and a second surface thereon;
   b. an elongated handle member having a shaft and an outer member and a first end and an opposite second end;
   c. a connecting member for rotatably and pivotally connecting said stabilizing device to said handle member, wherein said connecting member consists of a ball and socket member, where one of the ball member or said socket member is connected to the first end of the handle member and the other of the ball member or said socket member is connected to the second surface of the stabilizing member and wherein said ball member is removable from said socket member to enable said stabilizing device to be removed from said handle member; and
   d. wherein said handle member includes a tightener thereon wherein rotation of said tightener causes the relative movement of said shaft and said outer member on said handle member between locked and unlocked positions, wherein rotatable and pivotal movement of said stabilizing device with respect to said handle member is allowed in said unlocked position and prevented in said locked position.

20. An apparatus for stabilizing a predetermined area of a heart, the apparatus comprising:
   a. a stabilizing device for stabilizing a predetermined area of a heart, the stabilizing device having a first surface sized to contact the predetermined area of the heart of a patient and a second surface thereon;
   b. an elongated handle member having a shaft and an outer member and a first end and an opposite second end;
   c. a connecting member for rotatable and pivotally connecting said stabilizing device to said handle member, wherein said connecting member consists of a ball and socket member, where one of the ball member or said socket member is connected to the first end of the handle member and the other of the ball member or said socket member is connected to the second surface of the stabilizing member and wherein said ball member is removable from said socket member to enable said stabilizing device to be removed from said handle member; and
   d. wherein said handle member includes a tightener thereon wherein rotation of said tightener causes the relative movement of said shaft and said outer member on said handle member between engaged and disengaged positions, wherein removal of said stabilizing device with respect to said handle member is allowed in said disengaged position and prevented in said engaged position.

21. The apparatus of claim 20, wherein said handle member includes said tightener operatively connected to said second end thereof.

22. An apparatus for stabilizing a predetermined area of a heart, the apparatus comprising:
   a. a stabilizing device having a first surface sized to contact the predetermined area of the heart of a patient and a second surface thereon;
   b. an elongated handle member having a first end and an opposite second end;
   c. a connecting member for connecting said second surface of said stabilizing device to said first end of said handle member, wherein said stabilizing device is removable from said first end of said handle member;
   d. a rib retractor; and
   e. a swivel head having first and second portions thereon for connecting the handle member to the rib retractor.

23. The apparatus of claim 22, wherein said connecting member includes a selective locking mechanism therein to allow for the selective locking of said stabilizing device with respect to said handle member.

24. The apparatus of claim 22, wherein said handle member includes an outer member and a longitudinally extending bore extending between said first and second ends thereof and a shaft extending through said bore wherein said shaft and said outer member are movable with respect to each other to allow for the selective locking of said stabilizing device with respect to said handle member.

25. The apparatus of claim 22, wherein said handle member includes a tightener thereon wherein rotation of said tightener causes the relative movement of a shaft and an outer member on said handle member between locked and unlocked positions wherein movement of said stabilizing device with respect to said handle member is allowed in said unlocked position and prevented in said locked position.

26. The apparatus of claim 22, wherein said handle member includes a tightener thereon wherein rotation of said tightener causes the relative movement of a shaft and an outer member on said handle member between engaged and disengaged positions wherein removal of said stabilizing device with respect to said handle member is allowed in said disengaged position and prevented in said engaged position.

27. The apparatus of claim 22, wherein said handle member includes a tightener operately connected to said second end thereof.

28. The apparatus of claim 22, wherein said handle member includes a socket member on said first end thereof.

29. The apparatus of claim 22, wherein said connecting member includes a socket member therein and said socket member is an elongate member that includes an elongate slot extending through at least a portion thereof.

30. An apparatus for stabilizing a predetermined area of a heart, the apparatus comprising:

a. a stabilizing device having a first surface sized to contact the predetermined area of the heart of a patient and a second surface thereon;

b. an elongated handle member having a first end and an opposite second end;

c. a connecting member for connecting said second surface of said stabilizing device to said first end of said handle member, wherein said stabilizing device is removable from said handle member; and d. wherein said connecting member includes a ball member and a socket member and said socket member of said connecting member includes a sidewall having a slot therein and said slot is sized to releasably receive said ball member therein.

* * * * *

UNITED STATES PATENT AND TRADEMARK OFFICE
CERTIFICATE OF CORRECTION

PATENT NO.   : 6,254,535 B1  Page 1 of 1
DATED        : July 3, 2001
INVENTOR(S)  : Gregory R. Furnish and Christopher S. Looney It is certified that error appears in the above-identified patent and that said Letters Patent is hereby corrected as shown below:

<u>Title page,</u>
Item [56], FOREIGN PATENT DOCUMENTS, add the following:
--     791,329     8/1997   (EP)
       791,330     8/1997   (EP)
       791,332     8/1997   (EP)
       792,620     9/1992   (EP)   --

OTHER PUBLICATIONS, replace "Correspondance" with -- Correspondence --;

Signed and Sealed this

Twelfth Day of November, 2002

*Attest:*

*Attesting Officer*

JAMES E. ROGAN
*Director of the United States Patent and Trademark Office*